United States Patent [19]

Krenzer

[11] 3,944,410
[45] Mar. 16, 1976

[54] SUBSTITUTED OXADIAZOLIDINE DIONE HERBICIDES

[75] Inventor: John Krenzer, Oak Park, Ill.

[73] Assignee: Velsicol Chemical Corporation, Chicago, Ill.

[22] Filed: Oct. 4, 1974

[21] Appl. No.: 511,960

Related U.S. Application Data

[62] Division of Ser. No. 707,402, Feb. 23, 1968, Pat. No. 3,872,298.

[52] U.S. Cl. .................................................. 71/92
[51] Int. Cl.² ......................................... A01N 9/22
[58] Field of Search ........................................ 71/92

[56] References Cited
UNITED STATES PATENTS

| | | | |
|---|---|---|---|
| 3,203,959 | 8/1965 | Huffman | 71/92 |
| 3,385,862 | 5/1968 | Metivier et al. | 71/92 |

*Primary Examiner*—Lewis Gotts
*Assistant Examiner*—Catherine L. Mills
*Attorney, Agent, or Firm*—Robert J. Schwarz; Dietmar H. Olesch

[57] ABSTRACT

New compounds of the formula

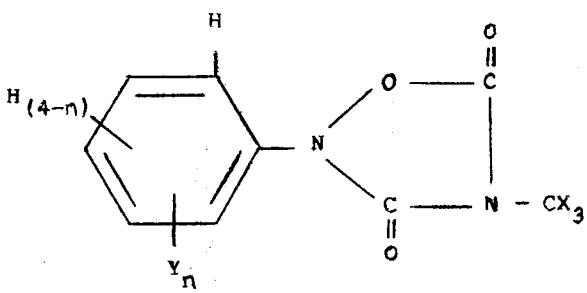

wherein X is halogen; Y is selected from the group consisting of alkyl, alkenyl, haloalkyl, halogen, alkoxy, nitro, alkylthio, alkylsulfoxide and alkylsulfone; and $n$ is an integer from 0 to 4, provided a maximum of two Y's are selected from the group consisting of nitro when $n$ is greater than two. A herbicidal composition comprising an inert carrier and, in a quantity toxic to weeds, a compound of the above description. A method of controlling weeds which comprises contacting said weeds with a herbicidal composition described.

7 Claims, No Drawings

SUBSTITUTED OXADIAZOLIDINE DIONE HERBICIDES

This application is a division of copending application Ser. No. 707,402 filed Feb. 23, 1968, now U.S. Pat. No. 3,872,298.

This invention relates to new compositions of matter and more particularly relates to compounds of the formula

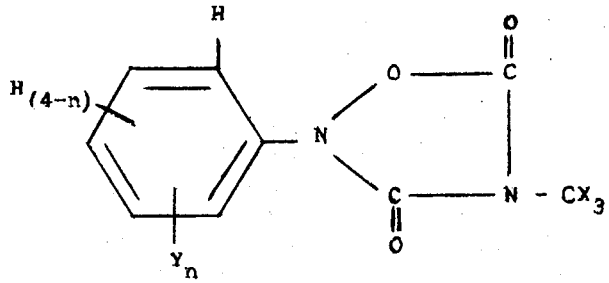

(I)

wherein X is halogen, Y is selected from the group consisting of alkyl, alkenyl, haloalkyl, halogen, alkoxy, nitro, alkylthio, alkylsulfoxide, and alkylsulfone; and $n$ is an integer from 0 to 4 provided a maximum of two Y's are nitro when $n$ is greater than two.

In a preferred embodiment of this invention X is selected from the group consisting of fluorine, chlorine and bromine; Y is selected from the group consisting of halogen, lower alkyl, lower alkenyl, lower haloalkyl, lower alkoxy, and nitro; and n is as heretofore described.

The compounds of the present invention are unexpectedly effective as pesticides and particularly as herbicides.

The new compounds of this invention can be readily prepared by reacting a urea of the formula

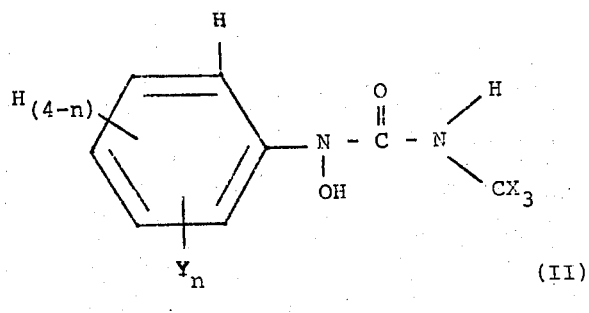

(II)

wherein X, Y and $n$ are as heretofore described, with an alkyl chloroformate such as ethyl chloroformate. The reaction can be conveniently carried out in aqueous base such as aqueous sodium hydroxide solution by adding the alkyl chloroformate to the urea at lower temperatures such as at 5° to 20°C. The addition is preferably performed with stirring and the stirring continued after the addition. The desired product can then be recovered from the reaction mixture by methods common to the art such as filtration, decantation, extraction, washing, drying, recrystallization and the like.

The compounds of this invention wherein at least one Y is selected from the group consisting of alkylsulfoxide and alkylsulfone can be prepared from the corresponding lower alkylthio compound by oxidation methods well known in the art.

The urea compounds of Formula II can be prepared readily from the corresponding N-arylhydroxylamine by reacting with an appropriate isocyanate of the formula $$X_3C - N = C = O$$

wherein X is as heretofore described. This reaction can be carried out by adding the isocyanate to a solution of the N-arylhydroxylamine in a suitable solvent such as diethyl ether. Low temperatures are preferred for this reaction such as from about 0° to 10°C. The resulting urea can be used in the reaction solution as such, or can be recovered therefrom by precipitation upon adding a diluent such as pentane followed by filtration and drying.

Exemplary of suitable urea compounds are 1-trifluoromethyl-3-phenyl-3-hydroxyurea, 1-trifluoromethyl-3-(4'-chlorophenyl)-3-hydroxyurea, 1-trichloromethyl-3-(3'-methylphenyl)-3-hydroxyurea, 1-trifluoromethyl-3-(3',4'-dichlorophenyl)-3-hydroxyurea, 1-trifluoromethyl-3-(3'-chloro-4'-methylphenyl)-3hydroxyurea, 1-tribromomethyl-3-(3'-ethyl-4'-nitrophenyl)-3-hydroxyurea, 1-trifluoromethyl-3-(4'-allylphenyl)-3-hydroxyurea, 1-trifluoromethyl-3-(4'-trifluoromethylphenyl)-3-hydroxyurea, 1-trifluoromethyl-3-(3'-methylthiophenyl)-3-hydroxyurea, 1-trichloromethyl-3-(3',5'-dinitrophenyl)-3-hydroxyurea, 1-trifluoromethyl-3-(2'-methyl-4'-nitrophenyl)-3hydroxyurea, 1-trifluoromethyl-3-(3'-methoxyphenyl)-3-hydroxyurea, 1-tribromomethyl-3-(3'-bromophenyl)-3-hydroxyurea and the like.

Exemplary N-aryl hydroxylamine compounds are 4-chlorophenyl hydroxylamine, 3-bromophenyl hydroxylamine, 3,5-dichlorophenyl hydroxylamine, 4-methylphenyl hydroxylamine, 4-nitrophenyl hydroxylamine, 3-trichloromethylphenyl hydroxylamine, 3-methoxyphenyl hydroxylamine, and the like.

Exemplary suitable isocyanates are trifluoromethyl isocyanate, trichloromethyl isocyanate, tribromomethyl isocyanate and triiodomethyl isocyanate.

The N-aryl hydroxylamines used in the above preparation of the ureas of the present invention can be prepared from the corresponding nitrobenzene.

The manner in which the compounds of the present invention can be prepared readily is illustrated in the following examples.

EXAMPLE 1

Preparation of 1Trifluoromethyl-3-phenyl-3-hydroxyurea

A solution of trifluoromethyl isocyanate (11.1 grams, 0.1 mol) in diethyl ether (35 ml) is added dropwise, with stirring to a solution of N-phenyl hydroxylamine (10.9 grams; 0.1 mol) in ether (60 ml) at room temperature. Stirring is continued for a period of about 1 hour resulting in a precipitate. Pentane is added to the mixture to form additional precipitate. The precipitate is then recovered by filtration, is washed and dried to yield 1-trifluoromethyl-3-phenyl-3-hydroxyurea.

EXAMPLE 2

Preparation of 2-Phenyl-4-trifluoromethyl)-1,2,4-oxadiazolidine-3,5-dione

1-Trifluoromethyl-3-phenyl-3-hydroxyurea (11 grams; 0.05 mol) is dissolved in a cooled (10°C) 2N aqueous sodium hydroxide solution (35 ml). Ethyl chloroformate (6 ml; 0.06 mol) is added dropwise at 10° to 15°C with stirring. Stirring is continued for a period of about ½ hour after the addition is completed resulting in the formation of a precipitate. The precipitate is recovered by filtration, washed with water and dried to yield 2-phenyl-4-trifluoromethyl-1,2,4-oxadiazolidine-3,5-dione.

EXAMPLE 3

Preparation of 1-Trifluoromethyl-3-(4'-fluorophenyl)-3-hydroxyurea p-Fluoronitrobenzene (14.1 grams; 0.1 mol) is dissolved in tetrahydrofuran (100 ml). Ten percent palladium on charcoal catalyst (0.1 gram) is added to the solution followed by hydrazine (6.0 ml; 0.1 mol), and the resulting mixture stirred at room temperature for about 48 hours with cooling as necessary. The reaction mixture, containing N-(4-fluorophenyl)hydroxylamine, is dried over anhydrous magnesium sulfate and filtered. To this solution is added trifluoromethyl isocyanate (11.1 grams; 0.1 mol) and the solution is stirred for about 15 minutes. The reaction mixture is concentrated by evaporation of solvent and the resulting precipitate is recovered by filtration to yield 1-trifluoromethyl-3-(4'-fluorophenyl)-3-hydroxyurea.

EXAMPLE 4

Preparation of 2-(4'-Fluorophenyl)-4-trifluoromethyl-1,2,4-oxadiazolidine-3,5-dione 1-Trifluoromethyl-3-(4'-fluorophenyl)-3-hydroxyurea (11.9 grams; 0.05 mol) is dissolved in dioxane (80 ml) and mixed with 2N aqueous sodium hydroxide (30 ml). Ethyl chloroformate (5.7 ml; 0.06 mol) is then added dropwise to the mixture at 10° to 15°C, with stirring, resulting in the formation of a precipitate. The precipitate is recovered by filtration, washed with water and dried to yield 2-(4'-fluorophenyl)-4-trifluoromethyl-1,2,4-oxadiazolidine-3,5-dione.

EXAMPLE 5

Preparation of 1-Trichloromethyl-3-(3',4'-dichlorophenyl)-3-hydroxyurea

A solution of trichloromethyl isocyanate (16 grams; 0.1 mol) in diethyl ether (40 ml) is added dropwise, with stirring, to a solution of N-(3,4-dichlorophenyl) hydroxylamine (17.8 grams; 0.1 mol) in diethyl ether (60 ml) at room temperature. Stirring is continued for a period of about 1 hour resulting in the formation of a precipitate. The precipitate is recovered by filtration, is washed and dried to yield 1-trichloromethyl-3-(3',4'-dichlorophenyl)-3-hydroxyurea.

EXAMPLE 6

Preparation of 2-(3',4'-Dichlorophenyl)-4-trichloromethyl-1,2,4-oxadiazolidine-3,5-dione 1-Trichloromethyl-3-(3',4'-dichlorophenyl)-3-hydroxyurea (16.9 grams; 0.05 mol) is dissolved in dioxane (75 ml) and mixed with 2N aqueous sodium hydroxide (30 ml). Ethyl chloroformate (5.7 ml; 0.06 mol) is then added dropwise to the mixture with stirring, resulting in the formation of a precipitate. The precipitate is recovered by filtration, washed with water and dried to yield 2-(3', 4'-dichlorophenyl)-4-trichloromethyl-1,2,4-oxadiazolidine-3,5-dione.

EXAMPLE 7

Preparation of 1-Trifluoromethyl-3-(3'-methylphenyl)-3-hydroxyurea

A solution of trifluoromethyl isocyanate (11.1 grams; 0.1 mol) in diethyl ether (50 ml) is added dropwise, with stirring, to a solution of N-(3-methylphenyl) hydroxylamine (12.3 grams; 0.1 mol) in diethyl ether (50 ml) at room temperature. Stirring is continued for a period of about 1 hour resulting in the formation of a precipitate. The precipitate is recovered by filtration, is washed and dried to yield 1-trifluoromethyl-3-(3'-methylphenyl)-3-hydroxyurea.

EXAMPLE 8 preparation of 2-(3'-Methylphenyl)-4-trifluoromethyl-1,2,4-oxadiazolidine-3,5-dione 1-Trifluoromethyl-3-(3'-methylphenyl)-3-hydroxyurea (11.7 grams; 0.05 mol) is dissolved in dioxane (75 ml) and mixed with 2N aqueous sodium hydroxide (30 ml). Ethyl chloroformate (5.7 ml; 0.06 mol) is then added dropwise to the mixture with stirring, resulting in the formation of a precipitate. The precipitate is recovered by filtration, is washed and dried to yield 2-(3'-methylphenyl)-4-trifluoromethyl-1,2,4-oxadiazolidine-3,5-dione.

EXAMPLE 9

Preparation of 2-(4'-Methylsulfinylphenyl)-4-trifluoromethyl-1,2,4-oxadiazolidine-3,5-dione A solution of 2-(4'-methylthiophenyl)-4-trifluoromethyl-1,2,4-oxadiazolidine-3,5-dione (29.2 grams; 0.10 mol) in acetone (200 ml) is charged into a glass reaction vessel equipped with a mechanical stirrer. Hydrogen peroxide (16 grams; 0.14 mol) is then slowly added, with stirring, at room temperature. Stirring is continued for a period of about 72 hours after the addition is completed. After this time the solvent is removed from the reaction mixture by evaporation resulting in a solid product. The product is washed, recrystallized, and dried to yield 2-(4'-methylsulfinyl-phenyl)-4-trifluoromethyl-1,2,4-oxadiazolidine-3,5-dione.

Other compounds within the scope of the present invention can be prepared in a manner similar to that detailed in the foregoing examples. Presented in the following examples are the essential ingredients required to prepare the indicated named compounds by the procedures heretofore described.

EXAMPLE 10

N-(3,4-Dimethylphenyl) hydroxylamine + trifluoromethyl isocyanate + sodium hydroxide + ethyl chloroformate = 2-(3',4'-dimethylphenyl)-4-trifluoromethyl-1,2,4-oxadiazolidine-3,5-dione.

EXAMPLE 11

N-(4-Nitrophenyl) hydroxylamine + trichloromethyl isocyanate + sodium hydroxide + ethyl chloroformate = 2-(4'-nitrophenyl)-4-trichloromethyl-1,2,4-oxadiazolidine-3,5-dione.

EXAMPLE 12

N-(4-Methylthiophenyl) hydroxylamine + tribromomethyl isocyanate + sodium hydroxide + ethyl chloroformate = 2-(4'-methylthiophenyl)-4-tribromomethyl-1,2,4-oxadiazolidine-3,5-dione.

EXAMPLE 13

N-(2-Allylphenyl) hydroxylamine + trifluoromethyl isocyanate + sodium hydroxide + ethyl chloroformate = 2-(2'-allylphenyl)-4-trifluoromethyl-1,2,4-oxadiazolidine-3,5-dione.

EXAMPLE 14

N-(3,4-Dichlorophenyl) hydroxylamine + trifluoromethyl isocyanate + sodium hydroxide + ethyl chloroformate = 2-(3',4'-dichlorophenyl)-4-trifluoromethyl-1,2,4-oxadiazolidine-3,5-dione.

EXAMPLE 15

N-(3-Methyl-4-chlorophenyl) hydroxylamine + trifluoromethyl isocyanate + sodium hydroxide + ethyl chloroformate = 2-(3'-methyl-4'-chlorophenyl)-4-trifluoromethyl-1,2,4-oxadiazolidine-3,5-dione.

EXAMPLE 16

N-(4-Trifluoromethylphenyl) hydroxylamine + trifluoromethyl isocyanate + sodium hydroxide + ethyl chloroformate = 2-(4'-trifluoromethylphenyl)-4-trifluoromethyl-1,2,4-oxadiazolidine-3,5-dione.

For practical use as herbicides the compounds of this invention are generally incorporated into herbicidal compositions which comprise an inert carrier and a herbicidally toxic amount of such a compound. Such herbicidal compositions, which can also be called formulations, enable the active compound to be applied conveniently to the site of the weed infestation in any desired quantity. These compositions can be solids such as dusts, granules, or wettable powders; or they can be liquids such as solutions, aerosols, or emulsifiable concentrates.

For example, dusts can be prepared by grinding and blending the active compound with a solid inert carrier such as the talcs, clays, silicas, pyrophyllite, and the like. Granular formulations can be prepared by impregnating the compound, usually dissolved in a suitable solvent, onto and into granulated carriers such as the attapulgites or the vermiculites, usually of a particle size range of from about 0.3 to 1.5 mm. Wettable powders, which can be dispersed in water or oil to any desired concentration of the active compound, can be prepared by incorporating wetting agents into concentrated dust compositions.

In some cases the active compounds are sufficiently soluble in common organic solvents such as kerosene or xylene so that they can be used directly as solutions in these solvents. Frequently, solutions of herbicides can be dispersed under super-atmospheric pressure as aerosols. However, preferred liquid herbicidal compositions are emulsifiable concentrates, which comprise an active compound according to this invention and as the inert carrier, a solvent and an emulsifier. Such emulsifiable concentrates can be extended with water and/or oil to any desired concentration of active compound for application as sprays to the site of the weed infestation. The emulsifiers most commonly used in these concentrates are nonionic or mixtures of nonionic with anionic surface-active agents. With the use of some emulsifier systems an inverted emulsion (water in oil) can be prepared for direct application to weed infestations.

A typical herbicidal composition according to this invention is illustrated by the following example, in which the quantities are in parts by weight.

EXAMPLE 17

Preparation of a Dust

| Product of Example 2 | 10 |
|---|---|
| Powdered Talc | 90 |

The above ingredients are mixed in a mechanical grinder-blender and are ground until a homogeneous, free-flowing dust of the desired particle size is obtained. This dust is suitable for direct application to the site of the weed infestation.

The compounds of this invention can be applied as herbicides in any manner recognized by the art. One method for the control of weeds comprises contacting the locus of said weeds with a herbicidal composition comprising an inert carrier and as an essential active ingredient, in a quantity which is herbicidally toxic to said weeds, a compound of the present invention. The concentration of the new compounds of this invention in the herbicidal compositions will vary greatly with the type of formulation and the purpose for which it is designed, but generally the herbicidal compositions will comprise from about 0.05 to about 95 percent by weight of the active compounds of this invention. In a preferred embodiment of this invention, the herbicidal compositions will comprise from about 5 to about 75 percent by weight of the active compound. The compositions can also comprise such additional substances as other pesticides, such as insecticides, nematocides, fungicides, and the like; stabilizers, spreaders, deactivators, adhesives, stickers, fertilizers, activators, synergists, and the like.

The compounds of the present invention are also useful when combined with other herbicides and/or defoliants, dessicants, growth inhibitors, and the like in the herbicidal compositions heretofore described. These other materials can comprise from about 5% to about 95% of the active ingredients in the herbicidal compositions. Use of combinations of these other herbicides and/or defoliants, dessicants, etc. with the compounds of the present invention provide herbicidal compositions which are more effective in controlling weeds and often provide results unattainable with separate compositions of the individual herbicides. The other herbicides, defoliants, dessicants and plant growth inhibitors, with which the compounds of this invention can be used in the herbicidal compositions to control weeds, can include chlorophenoxy herbicides such as 2,4-D, 2,4,5-T, MCPA, MCPB, 4(2,4-DB), 2,4-DEB, 4-CPB, 4-CPA, 4CPP, 2,4,5-TB, 2,4,5-TES, 3,4-DA, silvex and the like; carbamate herbicides such as IPC, CIPC, swep, barban, BCPC, CEPC, CPPC, and the like; thiocarbamate and dithiocarbamate herbicides such as CDEC, metham sodium, EPTC, diallate, PEBC, perbulate, vernolate and the like; substituted urea herbicides such as norea, siduron, dichloral urea, chloroxuron, cycluron, fenuron, monuron, monuron TCA, diuron, linuron, monolinuron, neburon, buturon, trimeturon and the like; symmetrical triazine herbicides such as simazine, chlorazine, atratone, desmetryne, norazine, ipazine, prometryn, atrazine, trietazine, simetone, prometone, propazine, ametryne, and the like; chloroacetamide herbicides such as alpha-chloro-N,N-dimethylacetamide, CDEA, CDAA, alpha-chloro-N-isopropylacetamide, 2-chloro-N-isopropylacetanilide, 4-(chloroacetyl)morpholine, 1-(chloroacetyl)-piperidine, and the like; chlorinated aliphatic acid herbicides such as TCA, dalapon, 2,3-dichloropropionic acid, 2,2,3-TPA and the like, chlorinated benzoic acid and phenylacetic acid herbicides such as 2,3,6-TBA, 2,3,5,6-TBA, dicamba, tricamba, amiben, fenac, PBA, 2-methoxy-3,6-dichlorophenylacetic acid, 3-methoxy-2,6-dichlorophenylacetic acid, 2-methoxy-3,5,6-trichlorophenylacetic acid, 2,4-dichloro-3-nitrobenzoic acid and the like; and such compounds as aminotriazole, maleic hydrazide, phenyl mercuric acetate, endothal, biuret, technical chlordane, dimethyl 2,3,5,6-tetrachloroterephthalate, diquat, erbon, DNC, DNBP, dichlobenil, DPA, diphenamid, dipropalin, trifluralin, solan, dicryl, merphos, CMPA, o-S-dimethyl tetrachlorothioterephthalate, methyl 2,3,5,6-tetrachloro-N-methoxy-N-methylterephthalamate, 2-[(4-chloro-o-tolyl)-oxy]-N-methoxyacetamide, DSMA, MSMA, potassium azide, acrolein, benefin, bensulide, AMS, bromacil, bromoxynil, cacodylic acid, CMA, CPMF, cypromid, DCB, DCPA, dichlone, diphenatril, DMTT, DNAP, EBEP, EXD, HCA, ioxynil, IPX, isocil, potassium cyanate, MAA, MAMA, MCPES, MCPP, MH, molinate, NPA, OCH, paraquat, PCP, picloram, DPA, PCA, pyrichlor, sesone, terbacil, terbutol, TCBA, brominil, CP-50144, H-176-1, H-732, M-2901, planavin, sodium tetraborate, calcium cyanamid, DEF, ethyl xanthogen disulfide, sindone, sindone B, propanil and the like.

Such herbicides can also be used in the methods and compositions of this invention in the form of their salts, esters, amides, and other derivatives whenever applicable to the particular parent compounds.

Weeds are undesirable plants growing where they are not wanted, having no economic value, and interfering with the production of cultivated crops, with the growing of ornamental plants, or with the welfare of livestock. Many types of weeds are known, including annuals such as pigweed, lambsquarters, fixtail, crabgrass, wild mustard, field pennycress, ryegrass, goose-grass, chickweed, wild oats, velvet leaf, purslane, barnyard grass, smartweed, knotweed, cocklebur, wild buckwheat, kochia, medic, corn cockle, ragweed, sowthistle, coffee-weed, croton, cuphea, dodder, fumitory, groundsel, hemp nettle, knawel, spurge, spurry, emex, jungle rice, pondweed, dog fennel, carpetweed, morning glory, bedstraw, ducksalad and naiad; biennials such as wild carrot, matricaria, wild barley, campion, chamomile, burdock, mullein, round-leaved mallow, bull thistle, houndstongue, moth mullein, and purple star thistle; or perennials such as white cockle, perennial ryegrass, quackgrass, Johnson grass, Canada thistle, hedge bindweed, Bermuda grass, sheep sorrel, curly dock, nutgrass, field chickweed, dandelion, campanula, field bindweed, Russian knapweed, mesquite, toadflax, yarrow, aster, gromwell, horsetail, ironweed, sesbania, bulrush, cattail and winter-cress.

Similarly, such weeds can be classified as broadleaf or grassy weeds. It is economically desirable to control the growth of such weeds without damaging beneficial plants or livestock.

The new compounds of this invention are particularly valuable for weed control because they are toxic to many species and groups of weeds while they are relatively nontoxic to many beneficial plants. The exact amount of compound required will depend on a variety of factors, including the hardiness of the particular weed species, weather, type of soil, method of application, the kind of beneficial plants in the same area, and the like. Thus, while the application of up to only about one or two ounces of active compound per acre may be sufficient for good control of a light infestation of weeds growing under adverse conditions, the application of ten pounds or more of an active compound per acre may be required for good control of a dense infestation of hardy perennial weeds growing under favorable conditions.

The herbicidal activity of the new compounds of this invention can be illustrated by many of the established testing techniques known to the art, such as pre- and postemergence testing. In one pre-emergence test the compounds are formulated as aqueous emulsions of acetone solutions. These formulations are then sprayed on the surface of soil which has been seeded less than 24 hours earlier with weed seeds. After spraying the soil containers are kept under normal lighting conditions and supplied with heat as required and daily or more frequent watering. The weeds are observed for about 7 to about 20 days, and the degree of injury to the weeds is recorded. The results indicate that compounds of this invention possess a high order of herbicidal activity.

To demonstrate the post-emergence activity of the compounds of this invention, emulsifiable concentrates or solutions of various concentrations of the aforementioned active compounds are sprayed on the foliage of weeds that have attained a prescribed size. After spraying the weeds are maintained under normal lighting conditions and supplied with heat as required. The soil in which the weeds are growing is watered daily or more frequently. The weeds are observed periodically for up to 14 days or more and the severity of injury to the weeds is recorded. The results indicate that the compounds of this invention possess a high order of herbicidal activity.

What is claimed is:

1. A herbicidal composition comprising an inert carrier and, in a quantity toxic to weeds, a compound of the formula

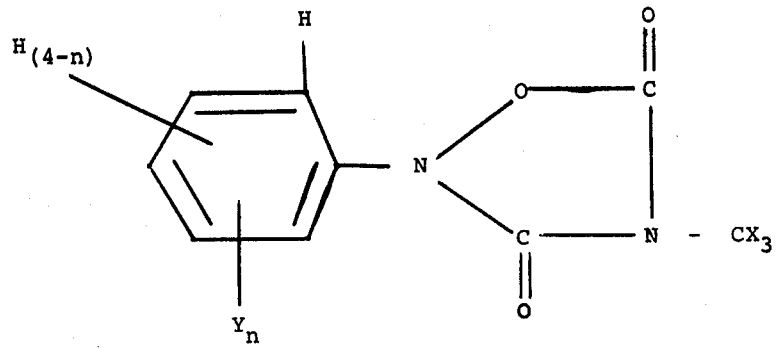

wherein X is selected from the group consisting of fluorine, chlorine and bromine; Y is selected from the group consisting of lower alkyl, lower alkenyl, lower haloalkyl, halogen, lower alkoxy and nitro; and $n$ is an integer from 0 to 4 provided a maximum of two Y's are selected from the group consisting of nitro when $n$ is greater than two.

2. A herbicidal composition of claim 1 wherein the compound is 2-phenyl-4-trifluoromethyl-1,2,4-oxadiazolidine-3,5-dione.

3. A herbicidal composition of claim 1 wherein the compound is 2-(3',4'-dichlorophenyl)-4-trifluoromethyl-1,2,4-oxadiazolidine-3,5-dione.

4. A herbicidal composition of claim 1 wherein the compound is 2-(3'-methylphenyl)-4-trifluoromethyl-1,2,4-oxadiazolidine-3,5-dione.

5. A herbicidal composition of claim 1 wherein the compound is 2-(4'-nitrophenyl)-4-trichloromethyl-1,2,4-oxadiazolidine-3,5-dione.

6. A herbicidal composition of claim 1 wherein the compound is 2-(3'-methyl-4'-chlorophenyl)-4-trifluoromethyl-1,2,4-oxadiazolidine-3,5-dione.

7. A method for the control of weeds which comprises contacting said weeds with a herbicidal composition of claim 1.

* * * * *